(12) United States Patent
Starkebaum et al.

(10) Patent No.: US 8,185,206 B2
(45) Date of Patent: May 22, 2012

(54) ELECTRICAL STIMULATION THERAPY TO PROMOTE GASTRIC DISTENTION FOR OBESITY MANAGEMENT

(75) Inventors: Warren L. Starkebaum, Plymouth, MN (US); Jiande Chen, Houston, TX (US)

(73) Assignee: Medtronic, Inc., Minneapolis, MN (US)

( * ) Notice: Subject to any disclaimer, the term of this patent is extended or adjusted under 35 U.S.C. 154(b) by 1222 days.

(21) Appl. No.: 11/804,312

(22) Filed: May 17, 2007

(65) Prior Publication Data

US 2007/0282387 A1  Dec. 6, 2007

Related U.S. Application Data

(60) Provisional application No. 60/800,931, filed on May 17, 2006.

(51) Int. Cl.
*A61N 1/18* (2006.01)

(52) U.S. Cl. .................. 607/40; 607/1; 607/2; 607/115; 607/116; 607/133

(58) Field of Classification Search .................. 607/1–2, 607/40, 115–116, 133
See application file for complete search history.

(56) References Cited

U.S. PATENT DOCUMENTS

| | | |
|---|---|---|
| 2,865,376 A | 12/1958 | Pellier et al. |
| 3,760,812 A | 9/1973 | Timm et al. |
| 4,444,207 A | 4/1984 | Robicsek |
| 4,475,560 A | 10/1984 | Tarjan et al. |
| 4,524,771 A | 6/1985 | McGregor et al. |
| 4,901,722 A | 2/1990 | Noguchi |
| 5,059,207 A | 10/1991 | Shah |
| 5,100,431 A | 3/1992 | Buster et al. |
| 5,188,104 A | 2/1993 | Wernicke et al. |
| 5,217,471 A | 6/1993 | Burkhart |
| 5,242,458 A | 9/1993 | Bendel et al. |
| 5,263,480 A | 11/1993 | Wernicke et al. |
| 5,292,344 A | 3/1994 | Douglas |
| 5,423,872 A | 6/1995 | Cigaina |
| 5,423,876 A | 6/1995 | Camps et al. |
| 5,433,728 A | 7/1995 | Kim |
| 5,450,739 A | 9/1995 | Bogart et al. |
| 5,484,404 A | 1/1996 | Schulman et al. |

(Continued)

FOREIGN PATENT DOCUMENTS

DE  44 02 058  4/1995

(Continued)

OTHER PUBLICATIONS

Notification Concerning Transmittal of International Preliminary Report on Patentability, for corresponding patent application No. PCT/US2007/011846, mailed Nov. 27, 2008, 7 pages.

(Continued)

*Primary Examiner* — Carl H Layno
*Assistant Examiner* — Deborah Malamud
(74) *Attorney, Agent, or Firm* — Jeffrey J. Hohenshell (57) ABSTRACT

The disclosure is directed to techniques for delivering electrical stimulation therapy to support obesity management. The electrical stimulation therapy is configured to cause at least partial gastric distention. Gastric distention tends to induce a sensation of fullness and thereby discourages excessive food intake by the patient. The electrical stimulation therapy may be delivered to the gastrointestinal tract of the patient by electrodes deployed by one or more implantable leads coupled to an electrical stimulator. The electrical stimulator delivers stimulation pulses having a pulse width in a range found to be effective in causing gastric distention.

35 Claims, 4 Drawing Sheets

U.S. PATENT DOCUMENTS

| | | | |
|---|---|---|---|
| 5,489,294 | A | 2/1996 | McVenes et al. |
| 5,540,730 | A | 7/1996 | Terry, Jr. et al. |
| 5,690,691 | A * | 11/1997 | Chen et al. ............... 607/40 |
| 5,716,392 | A | 2/1998 | Bourgeois et al. |
| 5,836,994 | A | 11/1998 | Bourgeois |
| 5,861,014 | A | 1/1999 | Familoni |
| 5,995,872 | A | 11/1999 | Bourgeois |
| 6,026,326 | A | 2/2000 | Bardy |
| 6,041,258 | A | 3/2000 | Cigaina et al. |
| 6,083,249 | A | 7/2000 | Familoni |
| 6,091,992 | A | 7/2000 | Bourgeois et al. |
| 6,097,984 | A | 8/2000 | Douglas |
| 6,098,672 | A | 8/2000 | Kiholm |
| 6,104,955 | A | 8/2000 | Bourgeois |
| 6,115,635 | A | 9/2000 | Bourgeois |
| 6,146,391 | A | 11/2000 | Cigaina |
| 6,216,039 | B1 | 4/2001 | Bourgeois |
| 6,238,423 | B1 * | 5/2001 | Bardy ............... 607/40 |
| 6,243,607 | B1 | 6/2001 | Mintchev et al. |
| 6,321,124 | B1 | 11/2001 | Cigaina |
| 6,327,503 | B1 | 12/2001 | Familoni |
| 6,449,511 | B1 * | 9/2002 | Mintchev et al. ............... 607/40 |
| 6,453,199 | B1 | 9/2002 | Kobozev |
| 6,510,332 | B1 | 1/2003 | Greenstein |
| 6,542,776 | B1 | 4/2003 | Gordon et al. |
| 6,564,101 | B1 * | 5/2003 | Zikria ............... 607/40 |
| 6,571,127 | B1 | 5/2003 | Ben-Haim et al. |
| 6,591,137 | B1 | 7/2003 | Fischell et al. |
| 6,600,953 | B2 | 7/2003 | Flesler et al. |
| 6,606,523 | B1 | 8/2003 | Jenkins |
| 6,615,084 | B1 | 9/2003 | Cigaina |
| 6,678,561 | B2 | 1/2004 | Forsell |
| 6,684,104 | B2 | 1/2004 | Gordon et al. |
| 6,895,278 | B1 | 5/2005 | Gordon |
| 6,993,391 | B2 | 1/2006 | Flesler et al. |
| 7,006,871 | B1 | 2/2006 | Darvish et al. |
| 7,120,497 | B2 | 10/2006 | Ben-Haim et al. |
| 7,177,693 | B2 | 2/2007 | Starkebaum |
| 7,221,978 | B2 | 5/2007 | Ben-Haim et al. |
| 7,330,753 | B2 | 2/2008 | Policker et al. |
| 7,502,649 | B2 | 3/2009 | Ben-Haim et al. |
| 7,512,442 | B2 | 3/2009 | Flesler et al. |
| 7,765,008 | B2 | 7/2010 | Ben-Haim et al. |
| 2002/0072780 | A1 | 6/2002 | Foley |
| 2002/0161414 | A1 | 10/2002 | Flesler et al. |
| 2002/0198470 | A1 | 12/2002 | Imran et al. |
| 2003/0009202 | A1 | 1/2003 | Levine |
| 2003/0018367 | A1 | 1/2003 | DiLorenzo |
| 2003/0054463 | A1 | 3/2003 | Baker et al. |
| 2004/0088022 | A1 | 5/2004 | Chen |
| 2004/0088023 | A1 | 5/2004 | Imran et al. |
| 2004/0162595 | A1 | 8/2004 | Foley |
| 2004/0193229 | A1 | 9/2004 | Starkebaum et al. |
| 2004/0236381 | A1 | 11/2004 | Dinsmoor et al. |
| 2004/0236382 | A1 | 11/2004 | Dinsmoor et al. |
| 2005/0021101 | A1 | 1/2005 | Chen et al. |
| 2005/0033375 | A1 | 2/2005 | Marchal et al. |
| 2005/0131486 | A1 | 6/2005 | Boveja et al. |
| 2005/0137643 | A1 | 6/2005 | Mintchev |
| 2005/0149141 | A1 | 7/2005 | Starkebaum |
| 2005/0209653 | A1 | 9/2005 | Herbert et al. |
| 2005/0222637 | A1 | 10/2005 | Chen |
| 2005/0222638 | A1 | 10/2005 | Foley et al. |
| 2005/0240239 | A1 | 10/2005 | Boveja et al. |
| 2005/0245957 | A1 | 11/2005 | Starkebaum et al. |
| 2006/0058856 | A1 | 3/2006 | Morrell |
| 2006/0085045 | A1 | 4/2006 | Harel et al. |
| 2006/0167498 | A1 | 7/2006 | DiLorenzo |
| 2006/0184207 | A1 | 8/2006 | Darvish et al. |
| 2006/0257444 | A1 | 11/2006 | Tropsha et al. |
| 2006/0257445 | A1 | 11/2006 | Tropsha et al. |
| 2006/0257446 | A1 | 11/2006 | Tropsha et al. |
| 2007/0027493 | A1 | 2/2007 | Ben-Haim et al. |
| 2007/0060812 | A1 | 3/2007 | Harel et al. |
| 2007/0104754 | A1 | 5/2007 | Sterling et al. |
| 2007/0104755 | A1 | 5/2007 | Sterling et al. |
| 2007/0150021 | A1 | 6/2007 | Chen et al. |
| 2007/0162084 | A1 | 7/2007 | Chen et al. |
| 2007/0282387 | A1 | 12/2007 | Starkebaum |
| 2007/0299320 | A1 | 12/2007 | Policker et al. |
| 2008/0058871 | A1 | 3/2008 | Libbus et al. |
| 2008/0178684 | A1 | 7/2008 | Spehr |
| 2009/0076561 | A1 | 3/2009 | Libbus et al. |
| 2009/0088817 | A1 | 4/2009 | Starkebaum |
| 2009/0118797 | A1 | 5/2009 | Kliger et al. |
| 2009/0204063 | A1 | 8/2009 | Policker et al. |
| 2009/0281449 | A1 | 11/2009 | Thrower et al. |
| 2010/0228105 | A1 | 9/2010 | Policker et al. |
| 2010/0228313 | A1 | 9/2010 | Starkebaum et al. |

FOREIGN PATENT DOCUMENTS

| | | |
|---|---|---|
| WO | WO 97/41921 | 11/1997 |
| WO | WO 02/26317 A1 | 4/2002 |
| WO | 02087657 | 11/2002 |
| WO | WO2009/045294 A1 | 4/2009 |
| WO | WO2009/097542 A2 | 8/2009 |

OTHER PUBLICATIONS

U.S. Patent Application entitled "Tachygastrial Electrical Stimulation", U.S. Appl. No. 11/058,572, filed Feb. 15, 2005.

Yong Lei et al., "Effects and Mechanisms of Implantable Gastric Stimulation on Gastric Distention in Conscious Dogs," Obesity Surgery, vol. 15, pp. 528-533, 2005.

Thirteenth International Workshop on Electrogastrography, Meeting-At-A-Glance, The Feinberg Pavilion, Northwestern University Medical Center, Chicago, Illinois, May 18-19, 2005, 58 pages.

Personalized Itinerary Planner and Abstract Book, DDW, May 20-25, 2006, 127 pages.

Hui Ouyang et al., "Gastric or intestinal electrical stimulation-induced increase in gastric volume is correlated with reduced food intake," Scandinavian Journal of Gastroenterology, vol. 41, pp. 1261-1266, 2006.

Luo et al., "Effects and Mechanisms of Gastric Electrical Stimulation on Gastric Tone in Rats", VA Research Foundation, Oklahoma City, OK, USA, 1 page, submitted for Digestive Disease Week 2006, Los Angeles Convention Center, May 20-25, 2006, (see also "DDW 2006 Rules for Abstract Submission", Digestive Disease Week 2006, Los Angeles Convention Center, May 20-25, 2006, 3 pages.).

Chen et al., "Gastric Electrical Stimulation for Obesity: is there a need for a new generation device?", VA Research Foundation, Oklahoma City, OK, USA, 1 page, submitted for Digestive Disease Week 2006, Los Angeles Convention Center, May 20-25, 2006, (see also "DDW 2006 Rules for Abstract Submission", Digestive Disease Week 2006, Los Angeles Convention Center, May 20-25, 2006, 3 pages.).

"DDW 2006 Rules for Abstract Submission", Digestive Disease Week 2006, Los Angeles Convention Center, May 20-25, 2006, 3 pages.

Chen et al., "Electrical Pacing Accelerates Intestinal Transit Slowed by Fat-Induced Ileal Brake", Digestive Diseases and Sciences, vol. 48, No. 2, Feb. 2003, pp. 251-256.

Valerio Cigaina, MD., "Implantable Gastric Stimulation for the Treatment of Morbid Obesity", Transneuronix, Inc., Revision 1, Oct. 3, 1999, 12 pages.

Valerio Cigaina, MD., "Implantable Gastric Stimulation for the Treatment of Morbid Obesity", Transneuronix, Inc., Revision 2, Nov. 1, 1999, 11pages.

Chen et al. "Electrical Pacing Accelerates Intestinal Transit Slowed by Fat-Induced Ileal Brake," Digestive Diseases and Sciences, vol. 48, No. 2 (Feb. 2003), pp. 251-256.

Sun et al. "Intestinal Electric Stimulation Decreases Fat Absorption in Rats: Therapeutic Potential for Obesity," Obesity Research, vol. 12, No. 8 (Aug. 2004), pp. 1235-1242.

Lin et al., "Electrical Stimulation of the Small Intestine in Dogs", Proceedings-19th International Conference-IEEE/EMBS, Oct. 30-Nov. 2, 1997, Chicago, IL., 4 pages.

Lei et al., "The effect of short-pulse gastric electrical stimulation (Enterra Therapy) on gastric tone varies with the sites and parameters of stimulation", Transneuronix Inc and Veterans Research Foundation, Oklahoma City, OK, May 2005, 1 page.

Ouyang et al., "Gastrointestinal Electrical Stimulation-Induced Increase in Gastric Volume Is Correlated with Reduced Food Intake", Transneuronix and Veterans Research & Education Foundation, Oklahoma City, OK, Mar. 2, 2006, 23 pages.

Notification of Transmittal of the International Search Report and the Written Opinion of the International Searching Authority or the Declaration, for corresponding patent application no. PCT/US2007/011846, mailed Dec. 4, 2007, 14 pages.

Lei Yong et al., "Gastric electrical stimulation induced gastric distention in obese rats," BIOSIS/BIOSIS, XP-002579955, Apr. 28, 2010, 2 pages.

Zhang Jing et al., "Central neuronal mechanisms of GES and effects of stimulation parameters and locations in regular and diet-induced obese rats," BIOSIS/BIOSIS, XP-002579956, Apr. 28, 2010, 2 pages.

Dickens et al., "Identification of rhythmically active cells in guinea-pig stomach," Journal of Physiology, vol. 514, No. 2, pp. 515-531 (Jan. 1999).

Huizinga, "Gastrointestinal Peristalsis: Joint Action of Enteric Nerves, Smooth Muscle, and Interstitial Cells of Cajal," Microscopy Research and Technique, vol. 47, No. 4, pp. 239-247 (Dec. 1999).

Vantrappen et al., "Gastrointestinal Motility Disorders," Digestive Diseases and Sciences, vol. 31, No. 9, pp. 5S-25S, (Sep. 1986 Supplement).

Shepherd et al., "Electrical stimulation of the auditory nerve: II. Effect of stimulus waveshape on single fibre response properties," Hearing Research 130 (1999): 171-188.

MacHerey et al., "Asymmetric Pulses in Cochlear Implants: Effects of Pulse Shape, Polarity, and Rate," JARO 7: 255-266 (2006), pp. 253-266.

Rubinstein et al., "Analysis of Monophasic Biphasic Electrical Stimulation of Nerve," IEEE Transactions on Biomedical Engineering, vol. 48, No. 10, Oct. 2001, pp. 1065-1070.

Shepherd et al., "Chronic Electrical Stimulation of the Auditory Nerve using Non-charge-balanced Stimuli," Acta Otolayngol (Stockh) 1999;119:674-684.

Van Wieringen, "Effects of waveform shape on human sensitivity to electrical stimulation of the inner ear," Hearing Research 200 (2005), pp. 73-86.

McIntyre et al., "Extracellular Stimulation of Central Neurons: Influence of Stimulus Waveform and Frequency on Neuronal Output," J Neurophysiol 88: 1592-1604, 2002.

Eddington et al., "Speech Processors for Auditory Prostheses," NIH Contract NO1-DC-2-1001, Final Progress Report, Jan. 1, 2002-Jun. 30, 2005, 14 pp.

Carlyon et al., "Effect of inter-phase gap on the sensitivity of cochlear implant users to electrical stimulation," Hearing Research 205 (2005), 210-224.

Miller et al., "Electrically evoked single-fiber action potentials from cat: responses to monopolar, monophasic stimulation," Hearing Research 130 (1999), 197-218.

Stylopoulos et al., "Roux-en-Y gastric bypass enhances energy expenditure and extends lifespan in diet-induced obese rats," Obesity, 2009 17(10):1839-47.

Kanno et al., "Rat gastric banding model for bariatric surgery," J Nippon Med Sch. 2008 75(4):202-6.

Endo et al., "An obese rat model of bariatric surgery with gastric banding," Obes Surg. 2007 17(6):815-9.

Monteiro et al., "A rat model of restrictive bariatric surgery with gastric banding," Obes Surg 2006 16(1):48-51.

Monteiro et al., "Rats submitted to gastric banding are leaner and show distinctive feeding patterns," Obes Surg. 2006 16(5):597-602.

Monteiro et al., "Increase in ghrelin levels after weight loss in obese Zucker rats is prevented by gastric banding," Obes Surg. 2007 17(12):1599-607.

Kampe et al., "A rodent model of adjustable gastric band surgery-implications for the understanding of underlying mechanisms," Obes Surg 2009 19(5):625-31.

Lei et al., "Effects of dual pulse gastric electrical stimulation on gastric tone and compliance in dogs," Digestive and Liver Disease, 2008, Dig Liver Dis (2008), doi:10.1016/j.dld.2008.07.312.

Liu et al., "Therapeutic potentials of a novel mthod of dual-pulse gastric electrdical stimulation for gastric dysrhythmia and symptoms of nausea and vomiting," The American Journal of Surgery 191 (2006): 255-261.

Qi et al., "Dual pulse intestinal electrical stimulation normalizes intestinal dysrhythmia and improves symptoms induced by vasopressin in fed state in dogs," Neurogastroenterol Motil (2007) 19: 411-418.

Song et al., "A novel method of 2-channel dual-pulse gastric electrical stimulation improves solid gastric emptying in dogs," Surgery 2008;143:72-8.

Chen, "Gastric Electrical Stimulation With Short Pulses Reduces Vomiting but not Dysrhythmias in Dogs," Gastroenterology 2003;124:401-409.

Chen et al., "Gastric electrical stimulation reduces visceral sensitivity in healthy canines," abstract presented at International Electrogastrography Society, 2005, 1 pg.

Lei et al., "Effects of dual pulses gastric electrical stimulation on gastric tone and compliance," abstract presented at International Electrogastrography Society, 2005, 1 pg.

Qi et al., "Normalization of intestinal dysrhythmia and improvement of symptoms with a novel method of dual pulse intestinal electrical stimulation in dogs," abstract presented at International Electrogastrography Society, 2005, 1 pg.

Song et al., "Effects of dual pulse gastric electrical stimulation on vasopressin-induced dysmotility in dogs," abstract presented at International Electrogastrography Society, 2005, 1 pg.

H. Abrahamsson, "Vagal Relaxation of the Stomach Induced from the Gastric Antrum", Acta physiol. scand. 1973, 89, pp. 406-414.

* cited by examiner

ELECTRICAL STIMULATION THERAPY TO PROMOTE GASTRIC DISTENTION FOR OBESITY MANAGEMENT

This application claims the benefit of U.S. provisional application No. 60/800,931, filed May 17, 2006, the entire content of which is incorporated herein by reference.

TECHNICAL FIELD

The invention relates to implantable medical devices and, more particularly, implantable medical devices for obesity management.

BACKGROUND

Obesity is a serious health problem for many people. Patients who are overweight often have problems with mobility, sleep, high blood pressure, and high cholesterol. Some other serious risks also include diabetes, cardiac arrest, stroke, kidney failure, and mortality. In addition, an obese patient may experience psychological problems associated with health concerns, social anxiety, and generally poor quality of life.

Certain diseases or conditions can contribute to additional weight gain in the form of fat, or adipose tissue. However, healthy people may also become overweight as a net result of excess energy consumption and insufficient energy expenditure. Reversal of obesity is possible but difficult. Once the patient expends more energy than is consumed, the body will begin to use the energy stored in the adipose tissue. This process will slowly remove the excess fat from the patient and lead to better health. Some patients require intervention to help them overcome their obesity. In these severe cases, nutritional supplements, prescription drugs, or intense diet and exercise programs may not be effective.

Surgical intervention is a last resort treatment for some obese patients who are considered morbidly obese. One common surgical technique is the Roux-en-Y gastric bypass surgery. In this technique, the surgeon staples or sutures off a large section of the stomach to leave a small pouch that holds food. Next, the surgeon severs the small intestine at approximately mid length and attaches the distal section of the small intestine to the pouch portion of the stomach. This procedure limits the amount of food the patient can ingest to a few ounces, and limits the amount of time that ingested food may be absorbed through the shorter length of the small intestine. While this surgical technique may be very effective, it poses significant risks of unwanted side effects, malnutrition, and death.

Electrical stimulation therapy is an alternative to surgical intervention, and may be effective in treating obesity either alone or in combination with diet and exercise. For electrical stimulation therapy, a patient is fitted with an implanted electrical stimulator that delivers electrical stimulation pulses to the patient's stomach via electrodes carried by one or more leads. The electrical stimulation therapy may be configured to induce a sensation of fullness or nausea in the patient, thereby discouraging excessive food intake. In addition, in some cases, the electrical stimulation therapy may be configured to increase gastric motility so that caloric absorption is reduced. Hence, electrical stimulation therapy may be effective in causing weight loss, by discouraging food intake and/or reducing caloric absorption.

SUMMARY

In general, the invention is directed to techniques for delivering electrical stimulation therapy to support obesity management. The electrical stimulation therapy is configured to cause at least partial gastric distention. Gastric distention tends to induce a sensation of fullness, i.e., satiety, and thereby discourages excessive food intake by the patient. The electrical stimulation therapy may be delivered to the gastrointestinal tract of the patient by electrodes deployed by one or more implantable leads coupled to an external or implantable electrical stimulator.

The electrical stimulator delivers stimulation pulses having a pulse width found to be effective in causing gastric distention. In addition, the pulse width may be selected to promote battery longevity in the implantable electrical stimulator. The pulse width also may be selected to avoid or reduce undesirable side effects. Hence, in some embodiments, the pulse width may be selected to balance effectiveness in causing gastric distention, power conservation, and avoidance or reduction of undesirable side effects.

In some embodiments, for example, the electrical stimulator delivers stimulation pulses with a pulse width greater than or equal to approximately 1 millisecond and, more preferably, greater than or equal to approximately 1.5 milliseconds. In another embodiment, still more preferably, the pulse width is greater than or equal to approximately 2 milliseconds. In other example embodiments, the electrical stimulator delivers stimulation pulses with a pulse width in a range of approximately 1 millisecond to approximately 50 milliseconds. In a further embodiment, the pulse width is in a range of approximately 1.5 milliseconds to approximately 10 milliseconds, more preferably approximately 2 milliseconds to approximately 10 milliseconds, more preferably approximately 2 milliseconds to 5 milliseconds, and still more preferably approximately 2.5 milliseconds to approximately 4 milliseconds. Hence, the pulse width may be greater than or equal to 2.5 milliseconds.

In one embodiment, the invention provides a method comprising generating electrical stimulation pulses with a pulse width of approximately 1 to 50 milliseconds, and applying the stimulation pulses to a gastrointestinal tract of a patient to cause gastric distention.

In another embodiment, the invention provides an implantable gastric stimulator comprising an electrical stimulation pulse generator that generates electrical stimulation pulses with a pulse width of approximately 1 to 50 milliseconds, and one or more electrodes, coupled to the pulse generator, that apply the stimulation pulses to a gastrointestinal tract of a patient to cause gastric distention.

In an additional embodiment, the invention provides a method comprising generating electrical stimulation pulses with a pulse width of approximately 2 to 5 milliseconds and a pulse rate of approximately 10 to 50 Hz, and applying the stimulation pulses to a gastrointestinal tract of a human patient via an implantable pulse generator and one or more electrodes associated with one or more implantable leads coupled to the implantable pulse generator to cause gastric distention.

In various embodiments, the invention may provide one or more advantages. For example, delivery of electrical stimulation therapy with a pulse width in a range of greater than or equal to approximately 1 millisecond, more preferably greater than or equal to approximately 1.5 milliseconds and, still more preferably greater than or equal to approximately 2 milliseconds may be effective in promoting gastric distention, e.g., to discourage excessive food intake by a patient and promote weight loss. A pulse width in a range of approximately 1 milliseconds to approximately 50 milliseconds, more preferably in a range of approximately 1.5 milliseconds to approximately 10 milliseconds, more preferably approximately 2 milliseconds to approximately 10 milliseconds, and even more preferably approximately 2 to 5 milliseconds, may be effective in causing gastric distention while promoting better power conservation. Electrical stimulation therapy with pulse widths in the above ranges may be more effective in conserving battery resources, relative to larger pulse widths, increasing longevity of an implanted electrical stimulation device. In addition, relative to larger pulse widths, electrical stimulation therapy having pulse widths in the ranges described above may be more effective in avoiding or reducing adverse side effects in the patient, which can detract from overall therapy and quality of life.

The details of one or more embodiments of the invention are set forth in the accompanying drawings and the description below. Other features, objects, and advantages of the invention will be apparent from the description and drawings, and from the claims.

DETAILED DESCRIPTION

In general, the invention is directed to techniques for delivering electrical stimulation therapy to support obesity management. The techniques may be embodied, for example, in an electrical stimulation method, an electrical stimulation device, or an electrical stimulation system. The electrical stimulation therapy is configured to cause at least partial gastric distention. In particular, the electrical stimulation therapy is delivered with stimulation pulses having a pulse width in a range found to be effective in causing gastric distention. In addition, the pulse width range may be selected to promote battery longevity in the implantable electrical stimulator. The pulse width also may be selected to avoid or reduce undesirable side effects in the patient. Hence, in some embodiments, the pulse width may be selected to balance effectiveness in causing gastric distention, power conservation, and avoidance or reduction of undesirable side effects.

As an example, the stimulation pulses may have a pulse width greater than or equal to approximately 1 millisecond and, more preferably, greater than or equal to approximately 1.5 milliseconds. In another embodiment, still more preferably, the pulse width is greater than or equal to approximately 2 milliseconds. In other embodiments, an electrical stimulator delivers stimulation pulses with a pulse width in a range of approximately 1 millisecond to approximately 50 milliseconds. In further embodiments, the pulse width is in a range of approximately 1.5 milliseconds to approximately 10 milliseconds, more preferably approximately 2 milliseconds to approximately 10 milliseconds, more preferably approximately 2 milliseconds to 5 milliseconds, and still more preferably approximately 2.5 milliseconds to approximately 4 milliseconds. Hence, the pulse width may be greater than or equal to 2.5 milliseconds.

Electrical stimulation having stimulation pulses with pulse widths in the above ranges may be effective in causing gastric distention and thereby discouraging excessive food intake and promoting weight loss while promoting better power conservation. In addition, electrical stimulation therapy with pulse widths in the above ranges may be more effective in conserving battery resources, relative to larger pulse widths, thereby increasing operational longevity of an implanted electrical stimulation device. In addition, relative to larger pulse widths, electrical stimulation therapy having pulse widths in the ranges described above may be more effective in avoiding or reducing adverse side effects in the patient. Examples of side effects caused by larger pulse widths include tremor, nausea, vomiting, pain and abdominal discomfort.

Figure 1:
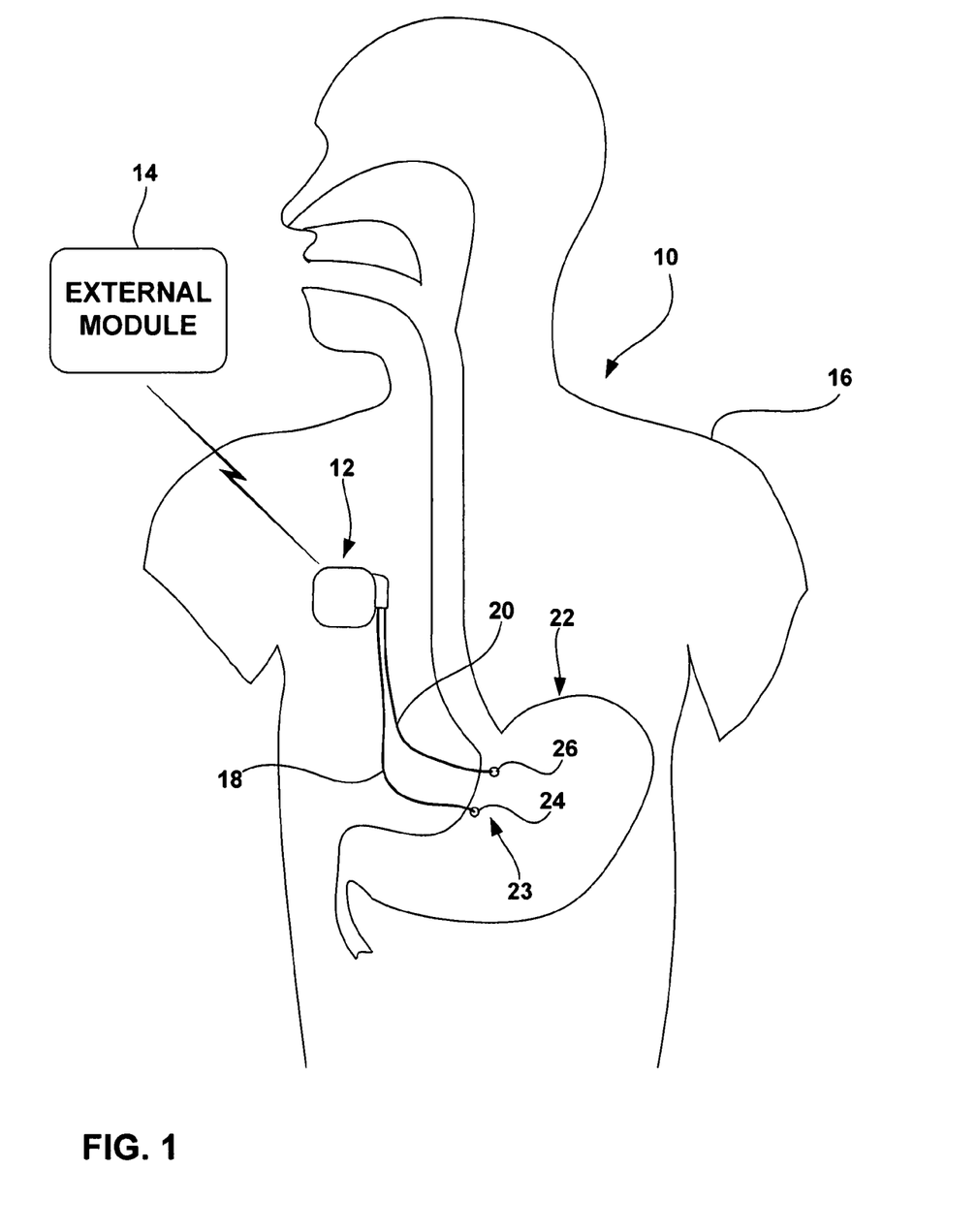
FIG. 1 is a schematic diagram illustrating an implantable gastric stimulation system.

FIG. 1 is a schematic diagram illustrating an implantable stimulation system 10. System 10 is configured to deliver electrical stimulation therapy to support obesity management. The electrical stimulation therapy is configured to cause at least partial gastric distention. Gastric distention generally refers to relaxation and expansion of a portion of the gastrointestinal tract, such as the stomach or small intestine. For purposes of illustration, the disclosure will generally focus on application of electrical stimulation therapy to the stomach, although stimulation may be applied elsewhere in the gastrointestinal tract.

As shown in FIG. 1, system 10 may include an implantable stimulator 12 and an external module 14, both shown in conjunction with a patient 16. Ordinarily, patient 16 is a human patient, as indicated in the example of FIG. 1. Stimulator 12 includes a pulse generator that generates electrical stimulation pulses. In some embodiments, system 10 may further include a drug delivery device that delivers drugs or other agents to the patient for obesity therapy. One or more implantable leads 18, 20 carry the electrical stimulation pulses from implanted stimulator 12 to stomach 22. In other embodiments, stimulator 12 may be an external stimulator coupled to percutaneously implanted leads. As a further embodiment, stimulator 12 may be formed as an RF-coupled system in which an external controller provides both control signals and inductively coupled power to an implanted pulse generator.

Leads 18, 20 each include one or more electrodes 24, 26 for delivery of the electrical stimulation pulses to stomach 22. Although the electrical stimulation pulses may be delivered to other areas within the gastrointestinal tract, such as the esophagus, duodenum, small intestine, or large intestine, delivery of stimulation pulses to stomach 22 will generally be described in this disclosure for purposes of illustration. In the example of FIG. 1, electrodes 24, 26 are placed in lesser curvature 23 of stomach 22. Alternatively, or additionally, electrodes 24, 26 could be placed in the greater curvature of stomach 22.

Gastric distention tends to induce a sensation of fullness and thereby discourages excessive food intake by the patient. The therapeutic efficacy of gastric electrical stimulation in managing obesity depends on the stimulation parameters and stimulation target. Electrical stimulation may have mechanical, neuronal and/or hormonal effects that result in a decreased appetite and increased satiety. In turn, decreased appetite results in reduced food intake and weight loss. Gastric distention, in particular, causes a patient to experience a sensation of satiety due to expansion of the stomach, biasing of stretch receptors, and signaling fullness to the central nervous system.

For patient 16 to lose weight, patient 16 must have a net energy such that energy expended is greater than or equal to energy consumed. Diet and exercise play a role in reducing energy consumption. As an alternative or supplement to diet and exercise, stimulator 12 delivers stimulation pulses to the gastrointestinal tract to cause gastric distention. Gastric distention tends to induce a sensation of fullness, and serves to limit food intake by patient 16. Implantable stimulator 12 is configured to deliver stimulation pulses having a pulse width in a range found to be particularly effective in causing gastric distention while promoting battery longevity in the implantable electrical stimulator.

In one embodiment, for example, stimulator 12 delivers stimulation pulses with a pulse width selected to promote gastric distention. As an example, the stimulation pulses delivered by stimulator 12 may have a pulse width greater than or equal to approximately 1 millisecond and, more preferably, greater than or equal to approximately 1.5 milliseconds. In another embodiment, still more preferably, the pulse width is greater than or equal to approximately 2 milliseconds. In other embodiments, an electrical stimulator delivers stimulation pulses with a pulse width in a range of approximately 1 millisecond to approximately 50 milliseconds. In further embodiments, the pulse width is in a range of approximately 1.5 milliseconds to approximately 10 milliseconds, more preferably approximately 2 milliseconds to approximately 10 milliseconds, more preferably approximately 2 milliseconds to 5 milliseconds, and still more preferably approximately 2.5 milliseconds to approximately 4 milliseconds. Hence, the pulse width may be greater than or equal to 2.5 milliseconds.

The pulse widths in the ranges identified above have been found to be long enough to cause substantial gastric distention. However, the pulse widths are selected to be sufficiently short so that excessive power consumption and adverse patient side effects may be avoided or reduced. In addition, diminishing gains in therapeutic effect may be perceived by patient 16 as the pulse widths become larger. Hence, the pulse width may be selected to balance therapeutic efficacy with reduced power consumption and side effects.

Patient 16 may be successfully treated with stimulation pulses having a range between 1 millisecond and 50 milliseconds. However, patient 16 may receive less efficacious therapy with pulse widths as low as 1 millisecond. In addition, larger pulse widths greater than or equal to 10 milliseconds may cause adverse effects to the patient that may be effective to treat obesity but detract from the patient's quality of life. Example adverse effects may include tremor, nausea, vomiting, gastrointestinal disorders, or other undesirable effects. Moreover, larger pulse widths generally result in a higher rate of power consumption.

For these reasons, patient 16 may be successfully treated with stimulation having pulse widths within a smaller range. For example, patient 16 may be successfully treated with stimulation having a pulse width between approximately 1.5 milliseconds and 10 milliseconds, between approximately 2 milliseconds and 10 milliseconds, between approximately 2 milliseconds and 5 milliseconds, and between approximately 2.5 milliseconds and 4 milliseconds. Pulse widths of 2 milliseconds and greater may be able to target excitable tissue with strength-duration characteristics not captured with pulse widths smaller than 2 milliseconds in some patients. However, in some cases, patient 16 may perceive adverse side effects with pulse widths substantially greater than or equal to approximately 5 milliseconds. Also, pulse widths greater than or equal to approximately 5 milliseconds may provide diminishing, additional therapeutic benefit over smaller pulse widths less than approximately 5 milliseconds. Accordingly, in these cases, patient 16 may be effectively treated with stimulation pulses having a pulse width between 2 milliseconds and 5 milliseconds, thereby balancing therapeutic efficacy, reduction in adverse side effects, and reduction in power consumption.

Battery longevity in an implantable stimulator is a paramount concern. Implantation of stimulator 12 in patient 16 requires surgery. Similarly, surgery is required for explanation of stimulator 12 in the event battery resources are exhausted, as well as for re-implantation of a replacement stimulator. To reduce the number of surgical operations, and associated pain, recovery time, and risks, it is desirable to preserve battery resources to the extent possible while ensuring therapeutic efficacy. Because shorter pulse widths may reduce power consumption while increasing battery longevity, delivery of stimulation pulses in particular pulse width ranges described in this disclosure may achieve therapeutic efficacy in causing gastric distention while promoting battery longevity.

With further reference to FIG. 1, at the outer surface of stomach 22, e.g., along the lesser curvature 23, leads 18, 20 penetrate into tissue such that electrodes 24 and 26 are positioned to deliver stimulation to the stomach. As mentioned above, the parameters of the stimulation pulses generated by stimulator 12 are selected to distend stomach 22 and thereby induce a sensation of fullness, i.e., satiety. In some embodiments, the parameters of the stimulation pulses also may be selected to induce a sensation of nausea. In each case, the induced sensation of satiety and/or nausea may reduce a patient's desire to consume large portions of food. Again, the stimulation pulses may be delivered elsewhere within the gastrointestinal tract, either as an alternative to stimulation of lesser curvature 23 of stomach 22, or in conjunction with stimulation of the lesser curvature of the stomach. As one example, stimulation pulses could be delivered to the greater curvature of stomach 22.

The pulse width may be selected so that electrical stimulation, when applied, causes at least a twenty-five percent increase in gastric volume relative to a baseline gastric volume, preferably at least a fifty percent increase in gastric volume, more preferably at least a seventy-five percent increase in gastric volume, and still more preferably at least a one-hundred percent increase in gastric volume. The increase in gastric volume may be measured relative to a baseline gastric volume, such as a preprandial (pre-meal) gastric volume, and may be measured within a selected area of the gastrointestinal tract. For example, the gastric volume may be measured within the stomach if electrical stimulation is applied to the stomach. Alternatively, the baseline and stimulation-induced gastric volume may be measured elsewhere within the gastrointestinal tract.

In addition to pulse width, the stimulation pulses are defined by other parameters including current or voltage amplitude, pulse rate, and duty cycle. In some embodiments, stimulation parameters may further include electrode combinations and polarities in the event leads 18, 20 provide multiple electrode positions. As an illustration, in addition to a pulse width in the ranges identified above, stimulator 12 may generate stimulation pulses having a current amplitude in a range of approximately 1 to 20 milliamps (mA), preferably approximately 2 to 10 mA, and more preferably approximately 3 to 6 mA. The pulse rate of the stimulation pulses may be in a range of approximately 0.05 to 50 Hertz (Hz), preferably approximately 1 to 50 Hz, more preferably approximately 10 to 50 Hz, and more preferably approximately 20 to 50 Hz. As described below, a substantial amount of distention may be produced for a pulse width of approximately 2 ms in combination with a pulse rate of approximately 40 Hz.

In addition, stimulator 12 may deliver the stimulation pulses with a duty cycle of approximately 50% ON/50% OFF, preferably 30% ON/70% OFF, and more preferably 20% ON/80% OFF. Duty cycle generally refers to the percentage of time that stimulator 12 is delivering stimulation pulses versus the percentage of time during which the stimulator is idle. During ON time, stimulator 12 delivers pulses according to a set of parameters such as amplitude, pulse rate and pulse width. During OFF time, stimulator 12 does not deliver stimulation pulses to patient 16. In addition, the duty cycle may include multiple levels of delivering stimulation and not delivering stimulation. For example, the duty cycle may include the amount of time pulses are delivered and the amount of time pulses are not delivered to patient 16 when the stimulator 12 is ON. Additionally, a higher level duty cycle includes the amount of time stimulator 12 is ON and OFF. In this manner, example stimulation therapy may have duty cycles that describe when stimulator 12 is ON and OFF in addition to cycles that describe the amount of time pulses are delivered to patient 16 during the ON period.

As one illustration, to cause gastric distention, stimulator 12 may deliver stimulation pulses with an amplitude of approximately 1 to 10 mA, a pulse width of approximately 2 to 10 milliseconds (ms), a pulse rate of approximately 1 to 60 Hz, and a duty cycle of approximately 25% ON/75% OFF. As another illustration, stimulator 12 may deliver stimulation pulses with an amplitude of approximately 3 to 6 mA, a pulse width of approximately 2 to 5 milliseconds (ms), a pulse rate of approximately 20 to 50 Hz, and a duty cycle of approximately 40% ON/60% OFF. In each case, stimulator 12 will cause substantial gastric distention and a sensation of fullness, resulting in reduced food intake and, ultimately, weight loss.

Implantable stimulator 12 may be constructed with a biocompatible housing, such as titanium, stainless steel, or a polymeric material, and is surgically implanted within patient 16. The implantation site may be a subcutaneous location in the side of the lower abdomen or the side of the lower back. Stimulator 12 is housed within the biocompatible housing, and includes components suitable for generation of electrical stimulation pulses. Stimulator 12 may be responsive to an external module 14 that generates control signals to adjust stimulation parameters. Although stimulator 12 is illustrated as implanted in the example of FIG. 1, in other embodiments, stimulator 12 may be an external stimulator coupled to percutaneous leads for either trial stimulation or chronic stimulation. As a further embodiment, stimulator 12 may be formed as an RF-coupled system in which an external controller provides both control signals and inductively coupled power to an implanted pulse generator.

Electrical leads 18 and 20 are flexible and include one or more internal conductors that are electrically insulated from body tissues and terminated with respective electrodes 24 and 26 at the distal ends of the respective leads. The leads may be surgically or percutaneously tunneled to stimulation sites on stomach 22. The proximal ends of leads 18 and 20 are electrically coupled to the pulse generator of stimulator 12 via internal conductors to conduct the stimulation pulses to stomach 22 via electrodes 24, 26.

Leads 18, 20 may be placed into the muscle layer or layers of stomach 22 via an open surgical procedure, or by laparoscopic surgery. Leads also may be placed in the mucosa or submucosa by endoscopic techniques or by an open surgical procedure. Electrodes 24, 26 may form a bipolar pair of electrodes. Alternatively, stimulator 12 may carry a reference electrode to form an "active can" arrangement, in which one or both of electrodes 24, 26 are unipolar electrodes referenced to the electrode on the pulse generator. The housing of implantable stimulator 12 may itself serve as a reference electrode. A variety of polarities and electrode arrangements may be used. Each lead 18, 20 may carry a single electrode or an array of electrodes, permitting selection of different electrode combinations and polarities among the leads for delivery of stimulation.

In addition to pulse width, as discussed above, the stimulation pulses delivered by implantable stimulator 12 are characterized by other stimulation parameters such as a voltage or current amplitude and pulse rate. Pulse width and the other stimulation parameters may be fixed, adjusted in response to sensed physiological conditions within or near stomach 22, or adjusted in response to patient or physician input entered via external module 14. For example, in some embodiments, patient 16 may be permitted to adjust stimulation amplitude, pulse width, or pulse rate and turn stimulation on and off via external module 14.

External module 14 transmits instructions to stimulator 12 via wireless telemetry. Accordingly, stimulator 12 includes telemetry electronics to communicate with external module 14. External module 14 may be a small, battery-powered, portable device that accompanies patient 16 throughout a daily routine. External module 14 may have a simple user interface, such as a button or keypad, and a display or lights. External module 14 may be a hand-held device configured to permit activation of stimulation and adjustment of stimulation parameters.

Alternatively, external module 14 may form part of a larger device including a more complete set of programming features including complete parameter modifications, firmware upgrades, data recovery, or battery recharging in the event stimulator 12 includes a rechargeable battery. External module 14 may be a patient programmer, a physician programmer, or a patient monitor. In some embodiments, external module 14 may be a general purpose device such as a cellular telephone, a wristwatch, a personal digital assistant (PDA), or a pager.

In some embodiments, system 10 may include multiple implantable stimulators 12 or multiple leads 18, 20 to stimulate a variety of regions of stomach 22. Stimulation delivered by the multiple stimulators may be coordinated in a synchronized manner, or performed without communication between stimulators. Also, the electrodes may be located in a variety of sites on the stomach, or elsewhere in the gastrointestinal tract, dependent on the particular therapy or the condition of patient 12.

Electrodes 24, 26 carried at the distal ends of lead 18, 20, respectively, may be attached to the wall of stomach 22 in a variety of ways. For example, the electrode may be formed as a gastric electrode that is surgically sutured onto the outer wall of stomach 22 or fixed by penetration of anchoring devices, such as hooks, barbs or helical structures, within the tissue of stomach 22. Also, surgical adhesives may be used to attach the electrodes. In some cases, the electrodes 24, 26 may be placed in the lesser curvature 23 on the serosal surface of stomach 22, within the muscle wall of the stomach, or within the mucosal or submucosal region of the stomach. Alternatively, or additionally, electrodes 24, 26 may be placed in the greater curvature of stomach 22 such that stimulation is delivered to the greater curvature.

In some embodiments, system 10 may include multiple implantable stimulators 12 to stimulate a variety of regions of stomach 22 or a variety of different regions in the gastrointestinal tract. Stimulation delivered by the multiple stimulators may be coordinated in a synchronized manner, or performed independently without communication between stimulators.

As an example, one stimulator may control other stimulators by wireless telemetry, all stimulators may be controlled by external module 14, or the stimulators may act autonomously subject to parameter adjustment or download by external module 14.

Figure 2:
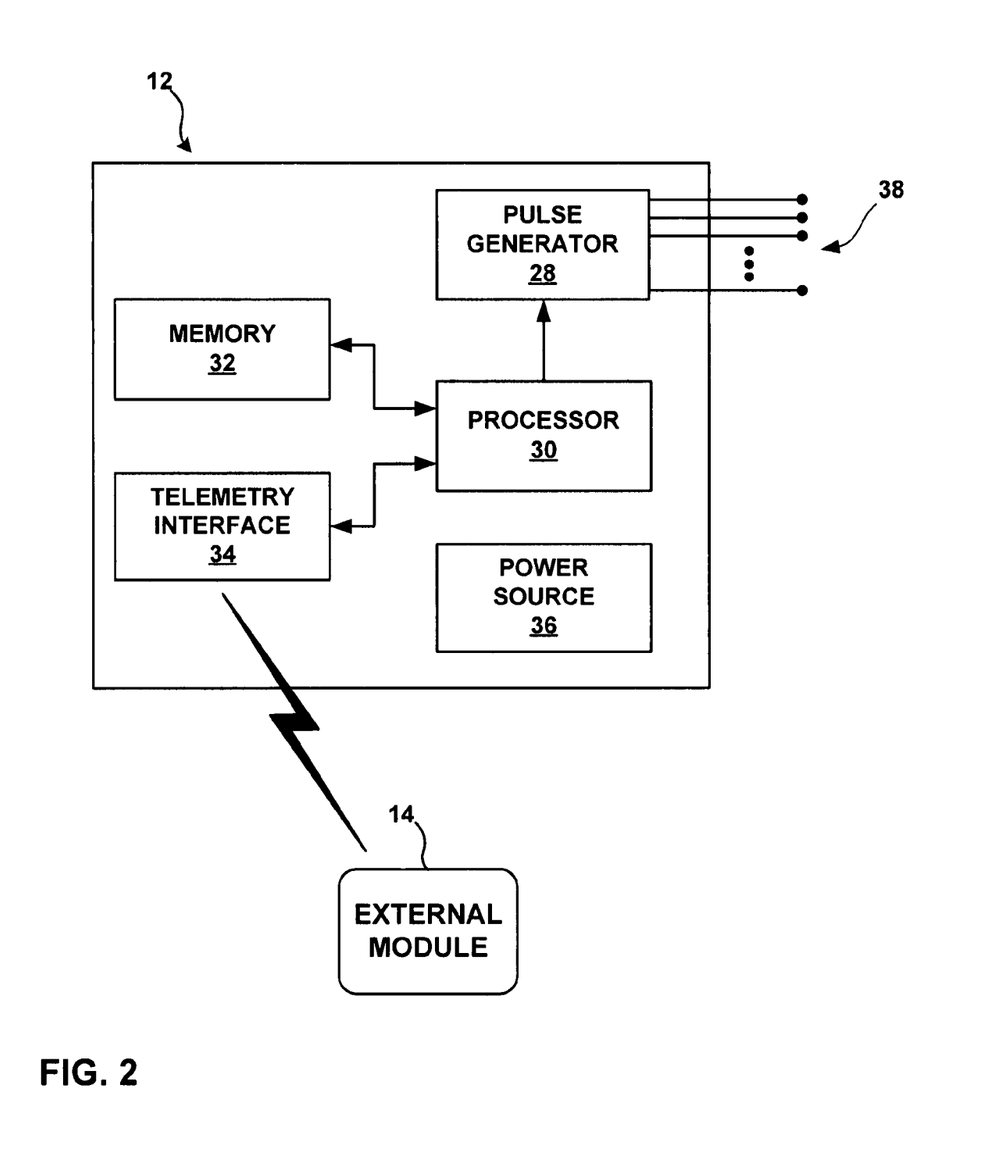
FIG. 2 is a block diagram illustrating exemplary components of an implantable gastric stimulator.

FIG. 2 is a block diagram illustrating implantable stimulator 12 in greater detail in accordance with an embodiment of the invention. In the example of FIG. 2, stimulator 12 includes pulse generator 28, processor 30, memory 32, wireless telemetry interface 34 and power source 36. In some embodiments, stimulator 12 may generally conform to the Medtronic Itrel 3 Neurostimulator, manufactured and marketed by Medtronic, Inc., of Minneapolis, Minn. However, the structure, design, and functionality of stimulator 12 may be subject to wide variation without departing from the scope of the invention as broadly embodied and described in this disclosure.

Processor 30 controls pulse generator 28 by setting and adjusting stimulation parameters such as pulse amplitude, pulse rate, pulse width and duty cycle. Processor 30 may be responsive to parameter adjustments or parameter sets received from external module 14 via telemetry interface 34. Hence, external module 14 may program stimulator 12 with different sets of operating parameters. In some embodiments, pulse generator 28 may include a switch matrix. Processor 30 may control the switch matrix to selectively deliver stimulation pulses from pulse generator 28 to different electrodes 38 carried by one or more leads 18, 20. In some embodiments, stimulator 12 may deliver different stimulation programs to patient 16 on a time-interleaved basis with one another.

Memory 32 stores instructions for execution by processor 30, including operational commands and programmable parameter settings. Memory 32 may include one or more memory modules constructed, e.g., as random access memory (RAM), read-only memory (ROM), non-volatile random access memory (NVRAM), electrically erasable programmable read-only memory (EEPROM), and/or FLASH memory. Processor 30 may access memory 32 to retrieve instructions for control of pulse generator 28 and telemetry interface 34, and may store information in memory 32, such as operational information.

Wireless telemetry in stimulator 12 may be accomplished by radio frequency (RF) communication or proximal inductive interaction of implantable stimulator 12 with external module 14 via telemetry interface 34. Processor 30 controls telemetry interface 34 to exchange information with external module 14. Processor 30 may transmit operational information and receive stimulation parameter adjustments or parameter sets via telemetry interface 34. Also, in some embodiments, stimulator 12 may communicate with other implanted devices, such as stimulators or sensors, via telemetry interface 34.

Power source 36 delivers operating power to the components of implantable stimulator 12. Power source 36 may include a battery and a power generation circuit to produce the operating power. In some embodiments, the battery may be rechargeable to allow extended operation. Recharging may be accomplished through proximal inductive interaction between an external charger and an inductive charging coil within implantable stimulator 12. In other embodiments, an external inductive power supply may transcutaneously power implantable stimulator 12 whenever stimulation therapy is to occur.

Implantable stimulator 12 is coupled to electrodes 38, which may correspond to electrodes 24 and 26 illustrated in FIG. 1, via one or more leads 18, 20. Implantable stimulator 12 provides stimulation therapy to the gastrointestinal tract of patient 16. Pulse generator 28 includes suitable pulse generation circuitry for generating a voltage or current waveform with a selected amplitude, pulse width, pulse rate, and duty cycle. In general, as described in this disclosure, the stimulation pulses generated by pulse generator 28 are formulated with pulse widths suitable to cause substantial gastric distention without excessive consumption of power provided by power source 36.

Figure 3:
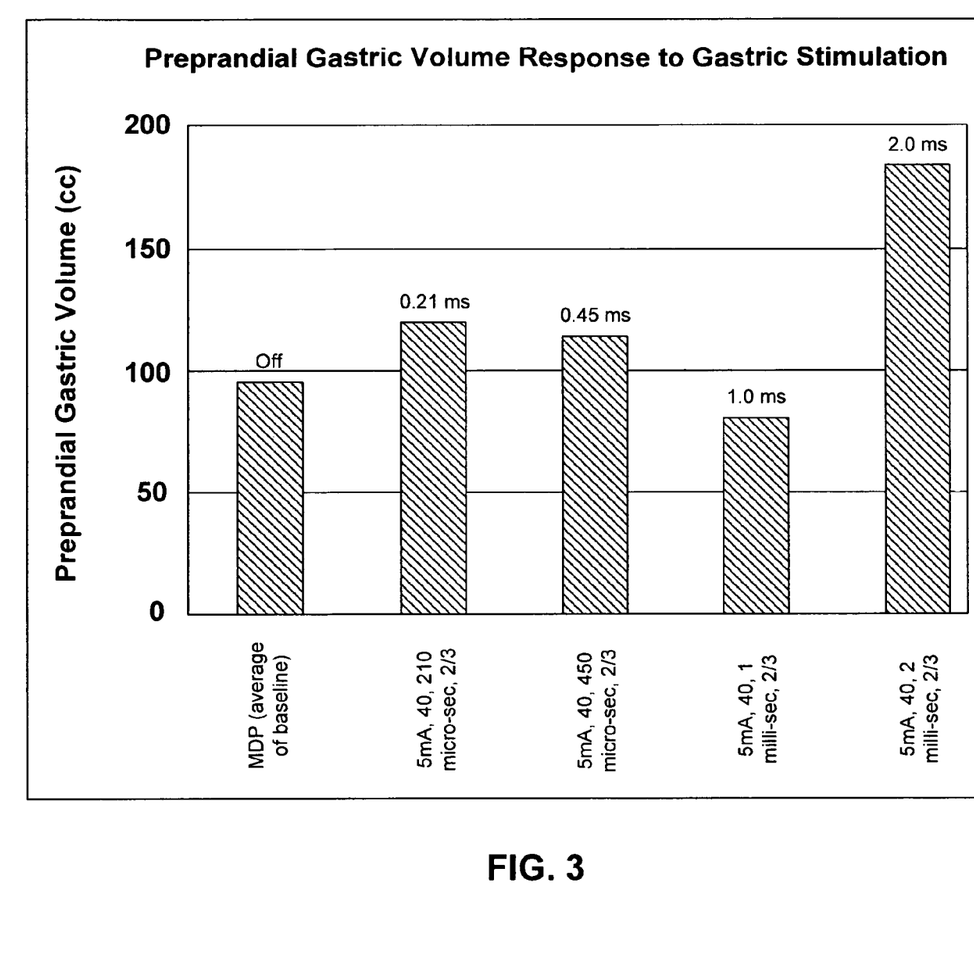
FIG. 3 is a graph illustrating gastric distention response to electrical stimulation therapy with different pulse widths.

FIG. 3 is a graph illustrating gastric distention response to electrical stimulation therapy with different pulse widths. In FIG. 3, the vertical axis represents the amount of gastric distention caused by different sets of stimulation pulse parameters in terms of preprandial (i.e., pre-meal) gastric volume in cubic centimeters (cc). The horizontal axis shows application of different stimulation parameter sets with substantially constant amplitude, pulse rate and duty cycle values, but varying pulse width values.

The results shown in FIG. 3 are from a canine study. To measure gastric distention, a gastric cannula with an attached balloon was placed in the proximal stomach via a percutaneous gastric port, approximately 10 centimeters (cm) proximal to the pylorus. The balloon was coupled to a barostat to measure gastric distention, e.g., as described in Yong Lei et al., Effects and Mechanisms of Implantable Gastric Stimulation on Gastric Distention in Conscious Dogs, Obesity Surgery, 15, pages 528-533, 2005.

With stimulation OFF, the baseline preprandial gastric volume was approximately 95 cc. In the graph, MDP refers to minimum distending pressure, which is the pressure just above the native abdominal pressure. With stimulation ON, gastric distention induced by electrical stimulation resulted in a gastric volume of approximately 120 cc upon application of stimulation pulses with a pulse amplitude of 5 milliamps (mA), pulse width of 0.21 milliseconds (210 microseconds), pulse rate of 40 Hz, and a duty cycle of 2 seconds ON and 3 seconds OFF (i.e., duty cycle of 40% ON and 60% OFF).

Gastric distention induced by electrical stimulation resulted in an increased gastric volume of approximately 110 cc upon application of stimulation pulses with a pulse amplitude of 5 milliamps (mA), pulse width of 0.45 milliseconds (450 microseconds), pulse rate of 40 Hz, and a duty cycle of 2 seconds ON and 3 seconds OFF (i.e., duty cycle of 40% ON and 60% OFF). Gastric distention induced by electrical stimulation resulted in an increased gastric volume of approximately 80 cc upon application of stimulation pulses with a pulse amplitude of 5 milliamps (mA), pulse width of 1.0 milliseconds, pulse rate of 40 Hz, and a duty cycle of 2 seconds ON and 3 seconds OFF (i.e., duty cycle of 40% ON and 60% OFF).

Notably, for a pulse width of 2 milliseconds, with a pulse amplitude of 5 milliamps (mA), pulse rate of 40 Hz, and a duty cycle of 2 seconds ON and 3 seconds OFF (i.e., duty cycle of 40% ON and 60% OFF), the gastric distention induced by electrical stimulation resulted in an increased gastric volume of approximately 180 cc. The approximate 180 cc volume caused by the 2 ms pulse width resulted in an increase in gastric volume of almost 100% relative to the baseline gastric volume of approximately 95 cc. Accordingly, as shown in FIG. 3, assuming common amplitudes, pulse rates and duty cycles, different pulse widths appear to have different impacts on the degree of gastric stimulation induced by electrical stimulation. In particular, to achieve more substantial gastric distention, it is desirable to increase the pulse width to a value greater than or equal to 1 millisecond (ms). More particularly, a more substantial degree of gastric distention was observed with a pulse width of 2 ms.

To avoid excessive power consumption, however, it is generally undesirable to apply stimulation pulses with very large pulse widths. Therefore, in accordance with an embodiment of the invention, stimulator 12 may be configured, programmed, or otherwise constructed to deliver stimulation pulses with pulse widths select to cause substantial gastric distention without consuming excessive amounts of power. As an example, the stimulation pulses delivered by stimulator 12 may have a pulse width greater than or equal to approximately 1 millisecond and, more preferably, greater than or equal to approximately 1.5 milliseconds. In another embodiment, still more preferably, the pulse width is greater than or equal to approximately 2 milliseconds. In other embodiments, an electrical stimulator delivers stimulation pulses with a pulse width in a range of approximately 1 millisecond to approximately 50 milliseconds. In further embodiments, the pulse width is in a range of approximately 1.5 milliseconds to approximately 10 milliseconds, more preferably approximately 2 milliseconds to approximately 10 milliseconds, more preferably approximately 2 milliseconds to 5 milliseconds, and still more preferably approximately 2.5 milliseconds to approximately 4 milliseconds.

Although higher pulse widths, e.g., 300 milliseconds, may cause as much or even more distention than pulse widths in the ranges described in this disclosure, the resulting power consumption is excessive, undermining device longevity due to the need for premature battery replacement. In addition, larger pulse widths may be more difficult to produce using existing electrical stimulation devices. Instead, larger pulse widths may require substantial redesign of pulse generator circuitry, which is generally undesirable. Further, larger pulse widths may cause undesirable adverse effects in patient 16 that prevent the overall therapy from being efficacious. Possible adverse effects may include tremors, nausea, vomiting, and/or other gastrointestinal changes. Various embodiments of the invention may provide a balance between therapeutic efficacy, power consumption, and pulse generator complexity.

Stimulator 12 may be configured to operate in either a voltage control mode or a current control mode. In a current control mode, a substantially constant current amplitude may be maintained for the pulses. For example, a constant current amplitude of approximately 5 mA is described in some of the examples in this disclosure. In a voltage control mode, a substantially constant voltage amplitude may be maintained for the pulses. For example, an appropriate voltage corresponding to approximately 5 mA can be determined by measuring the impedance of the leads and electrodes, and computing the voltage as voltage=current×impedance. Hence, stimulator 12 may deliver constant current or constant voltage stimulation pulses. As further illustration, example stimulation may be delivered over a 500 ohm impedance in patient 16. In this example, one embodiment may include a voltage range between 0.5 Volts (V) and 10V. In another embodiment, the voltage range may be between 1V and 5V. In an additional embodiment, the voltage range may be between 1.5V and 3V. These voltage ranges may be applicable to constant current amplitude embodiments or constant voltage embodiments.

Gastric stimulation has been shown to invoke a gastric distention response. Short pulse width (PW) stimulation results in a modest gastric distention response (GDR), while very wide pulse width stimulation results in maximal gastric distention response, but excessive power consumption. It is presumed that the GDR/PW curve has a sigmoid shape, which may allow for determination of the lowest power settings to invoke a desired GDR response.

In some embodiments, pulses may be delivered in bursts of pulses during the ON portion of the duty cycle. The pulse train may be delivered in a variety of different modes, such as a continuous mode, an asynchronous burst mode, or a synchronous burst mode. In a continuous mode, the pulse train is delivered relatively continuously over an active period in which stimulation is "ON." In an asynchronous burst mode, the pulse train is delivered in periodic bursts during the active period. The continuous mode and asynchronous burst mode may be considered open loop in the sense that they do not rely on synchronization with sensed events.

In a synchronous burst mode, the pulse train is delivered in bursts that are synchronized with a sensed event, such as a sensed physiological condition such as gastric contraction. In this sense, the synchronous burst mode may be viewed as a closed loop approach. For example, leads 18, 20 or different leads may carry one or more sensors, such as sense electrodes, piezoelectric electrodes, strain gauge sensors, accelerometers, pressure sensors, ultrasonic sensors or the like. Such sensors may sense physiological one or more conditions, such as gastric contractions, gastric nerve potentials, or gastric pressure, that indicate the intake of food. In response, stimulator 12 may activate stimulation to cause gastric distention and thereby discourage the intake of excessive amounts of food. Sensing may occur continuously, periodically, or intermittently, as therapy dictates. Information relating to the sensed conditions may be stored in memory within stimulator 12 or external module 14 for retrieval and analysis at a later time.

The active period for delivery of stimulation pulses each mode may be full-time, part-time, or subject to patient control. The active period is different from a duty cycle. The duty cycle applies during an active period, and represents the time that the stimulation is ON versus the time the stimulation is OFF during the active period. During an inactive period, no stimulation is delivered. For part-time activation, the stimulation may be activated for selected parts of the day. The selected parts of the day may coincide with meal times, physical activity times, sleep times, or other selected times, and be controlled using a clock within stimulator 12 or external module 14.

Additionally, or alternatively, patient 16 may control stimulator 12 via external module 16 to activate delivery of stimulation pulses, e.g., when the patient 16 intends to ingest a meal. Also, in some embodiments, patient 16 may be permitted to adjust one or more stimulation parameters such as amplitude, pulse width, pulse rate, or duty cycle, and turn stimulation on and off. In other cases, if the patient lacks sufficient discipline or capacity to effectively activate and adjust stimulation, stimulator 12 may operate without substantial patient intervention.

Figure 4:
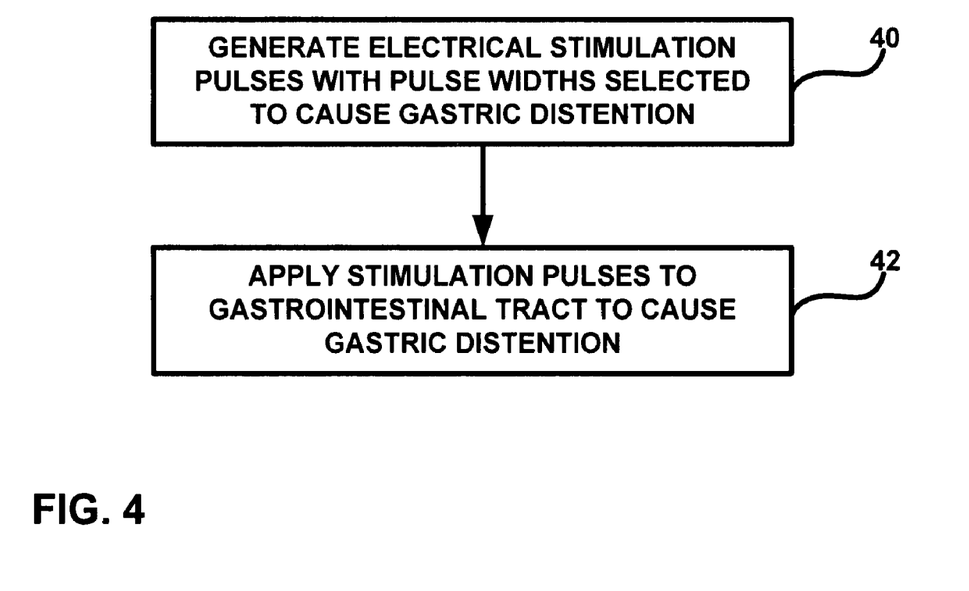
FIG. 4 is a flow diagram illustrating a method for delivering electrical stimulation having a pulse width selected to cause substantial gastric distention.

FIG. 4 is a flow diagram illustrating a method for delivering electrical stimulation having a pulse width selected to cause substantial gastric distention. As shown in FIG. 4, the method may include generating electrical stimulation pulses with pulse widths selected to cause gastric distention (40). As described in this disclosure, the stimulation pulses may have a pulse width greater than or equal to approximately 1 millisecond and, more preferably, greater than or equal to approximately 1.5 milliseconds. In another embodiment, still more preferably, the pulse width is greater than or equal to approximately 2 milliseconds. In other embodiments, an electrical stimulator delivers stimulation pulses with a pulse width in a range of approximately 1 millisecond to approximately 50 milliseconds. In further embodiments, the pulse width is in a range of approximately 1.5 milliseconds to approximately 10 milliseconds, more preferably approximately 2 milliseconds to approximately 10 milliseconds, more preferably approximately 2 milliseconds to 5 milliseconds, and still more preferably approximately 2.5 milliseconds to approximately 4 milliseconds. The method may further include applying the stimulation pulses to the gastrointestinal tract to cause gastric distention (42), e.g., via one or more electrodes carried by one or more implantable leads. The electrical stimulation pulses may be applied to the stomach, or to other areas within the gastrointestinal tract, such as the esophagus, duodenum, small intestine, or large intestine.

The techniques described in this disclosure may be implemented in hardware, software, firmware or any combination thereof. For example, various aspects of the techniques may be implemented within one or more microprocessors, digital signal processors (DSPs), application specific integrated circuits (ASICs), field programmable logic arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry.

When implemented in software, the functionality ascribed to the systems and devices described in this disclosure may be embodied as instructions on a computer-readable medium such as random access memory (RAM), read-only memory (ROM), non-volatile random access memory (NVRAM), electrically erasable programmable read-only memory (EEPROM), FLASH memory, magnetic media, optical media, or the like. The instructions are executed to support one or more aspects of the functionality described in this disclosure.

Various embodiments of the invention have been described. These and other embodiments are within the scope of the following claims.

The invention claimed is:

1. A method comprising:
generating electrical stimulation pulses with a pulse width of approximately 1 to 10 milliseconds; and
applying the stimulation pulses to a gastrointestinal tract of a patient to cause gastric distention.

2. The method of claim 1, wherein the pulse width of each of the stimulation pulses is greater than or equal to approximately 1.5 milliseconds.

3. The method of claim 1, wherein the pulse width of each of the stimulation pulses is greater than or equal to approximately 2 milliseconds.

4. The method of claim 1, wherein the pulse width of each of the stimulation pulses is in a range of approximately 2 to 5 milliseconds.

5. The method of claim 1, wherein the pulse width of each of the stimulation pulses is in a range of approximately 2.5 to 4 milliseconds.

6. The method of claim 1, wherein applying the stimulation pulses to a gastrointestinal tract comprises applying the stimulation pulses to a stomach of the patient.

7. The method of claim 6, wherein applying the stimulation pulses to a gastrointestinal tract comprises applying the stimulation pulses to a lesser curvature of the stomach of the patient.

8. The method of claim 1, wherein the stimulation pulses have an amplitude of approximately 1 to 20 milliamps and a pulse rate of approximately 1 to 60 Hertz.

9. The method of claim 1, wherein the stimulation pulses have an amplitude of approximately 1 to 10 milliamps and a pulse rate of approximately 10 to 50 Hz.

10. The method of claim 1, wherein the stimulation pulses have an amplitude of approximately 3 to 6 milliamps and a pulse rate of approximately 20 to 50 Hz.

11. The method of claim 1, wherein the pulse width of the stimulation pulses is selected to cause at least approximately a fifty percent increase in gastric volume.

12. The method of claim 1, wherein each of the stimulation pulses has a pulse width of approximately 2 to 5 milliseconds, a pulse rate of approximately 20 to 50 Hz, and a current amplitude of approximately 1 to 10 milliamps.

13. The method of claim 1, further comprising applying the stimulation pulses to the gastrointestinal tract via one or more electrodes associated with one or more implantable leads.

14. The method of claim 13, further comprising applying the stimulation pulses to the gastrointestinal tract via an implantable pulse generator and one or more electrodes associated with one or more implantable leads coupled to the implantable pulse generator.

15. The method of claim 1, wherein the patient is a human patient.

16. An implantable gastric stimulator comprising:
an electrical stimulation pulse generator that generates electrical stimulation pulses with a pulse width of approximately 1 to 10 milliseconds; and
one or more electrodes, coupled to the pulse generator, that apply the stimulation pulses to a gastrointestinal tract of a patient to cause gastric distention.

17. The device of claim 16, wherein the pulse width of each of the stimulation pulses is greater than or equal to approximately 1.5 milliseconds.

18. The device of claim 16, wherein the pulse width of each of the stimulation pulses is greater than or equal to approximately 2 milliseconds.

19. The device of claim 16, wherein the pulse width of each of the stimulation pulses is in a range of approximately 2 to 5 milliseconds.

20. The device of claim 16, wherein the pulse width of each of the stimulation pulses is in a range of approximately 2.5 to 4 milliseconds.

21. The device of claim 16, wherein the stimulation pulses have an amplitude of approximately 1 to 10 milliamps and a pulse rate of approximately 10 to 50 Hz.

22. The device of claim 16, wherein the stimulation pulses have an amplitude of approximately 3 to 6 milliamps, and a pulse rate of approximately 20 to 50 Hz.

23. The device of claim 16, wherein the pulse width of the stimulation pulses is selected to cause at least approximately a fifty percent increase in gastric volume.

24. The device of claim 16, wherein each of the stimulation pulses has a pulse width of approximately 2 to 5 milliseconds, a pulse rate of approximately 20 to 50 Hz, and a current amplitude of approximately 1 to 10 milliamps.

25. The device of claim 16, further comprising one or more implantable leads, coupled to the electrical stimulation pulse generator, that wherein the one or more implantable leads carry at least some of the electrodes.

26. The device of claim 25, wherein the electrical stimulation pulse generator is an implantable pulse generator.

27. The device of claim 16, wherein the stimulation pulses are selected to cause gastric distention in a human patient.

28. A method comprising:
generating electrical stimulation pulses with a pulse width of approximately 1 to 10 milliseconds and an amplitude of approximately 1 to 20 milliamps; and
applying the stimulation pulses to a gastrointestinal tract of a human patient to cause gastric distention.

29. The method of claim 28, wherein the pulse width of each of the stimulation pulses is in a range of approximately 2.5 to 4 milliseconds.

30. The method of claim 28, wherein applying the stimulation pulses to a gastrointestinal tract comprises applying the stimulation pulses to a stomach of the patient.

31. The method of claim 28, wherein each of the stimulation pulses has a pulse width of approximately 2.5 to 4 milliseconds, a pulse rate of approximately 20 to 50 Hz, and a current amplitude of approximately 1 to 10 milliamps.

32. An implantable gastric stimulator comprising:
- an electrical stimulation pulse generator that generates electrical stimulation pulses with a pulse width of approximately 1 to 10 milliseconds and an amplitude of approximately 1 to 20 milliamps; and
- one or more electrodes, coupled to the pulse generator, that apply the stimulation pulses to a gastrointestinal tract of a human patient to cause gastric distention.

33. The device of claim 32, wherein the pulse width of each of the stimulation pulses is in a range of approximately 2.5 to 4 milliseconds.

34. The device of claim 32, wherein applying the stimulation pulses to a gastrointestinal tract comprises applying the stimulation pulses to a stomach of the patient.

35. The device of claim 32, wherein each of the stimulation pulses has a pulse width of approximately 2.5 to 4 milliseconds, a pulse rate of approximately 20 to 50 Hz, and a current amplitude of approximately 1 to 10 milliamps.

\* \* \* \* \*

UNITED STATES PATENT AND TRADEMARK OFFICE
CERTIFICATE OF CORRECTION

PATENT NO. : 8,185,206 B2
APPLICATION NO. : 11/804312
DATED : May 22, 2012
INVENTOR(S) : Warren Starkebaum and Jiande Chen Page 1 of 1

It is certified that error appears in the above-identified patent and that said Letters Patent is hereby corrected as shown below:

In the Claims:

Col. 14, lines 49-50: "...pulse generator, that wherein..." should be "...pulse generator, wherein..."

Signed and Sealed this
Fourth Day of June, 2013

Teresa Stanek Rea
*Acting Director of the United States Patent and Trademark Office*